(12) United States Patent
Eckermann

(10) Patent No.: US 11,179,562 B1
(45) Date of Patent: Nov. 23, 2021

(54) SPINAL CORD STIMULATOR PADDLE APPLICATOR, NEUROSTIMULATION LEAD, AND STEERING MECHANISM

(71) Applicant: Jan Eckermann, Corona Del Mar, CA (US)

(72) Inventor: Jan Eckermann, Corona Del Mar, CA (US)

( * ) Notice: Subject to any disclaimer, the term of this patent is extended or adjusted under 35 U.S.C. 154(b) by 199 days.

(21) Appl. No.: 15/940,886

(22) Filed: Mar. 29, 2018

Related U.S. Application Data

(63) Continuation-in-part of application No. 15/087,316, filed on Mar. 31, 2016.

(60) Provisional application No. 62/181,546, filed on Jun. 18, 2015.

(51) Int. Cl.
*A61N 1/05* (2006.01)
*A61N 1/36* (2006.01)
*A61N 1/04* (2006.01)

(52) U.S. Cl.
CPC ....... *A61N 1/0553* (2013.01); *A61N 1/36062* (2017.08); *A61N 1/36071* (2013.01); *A61N 1/0456* (2013.01); *A61N 1/36146* (2013.01)

(58) Field of Classification Search
None
See application file for complete search history.

(56) References Cited

U.S. PATENT DOCUMENTS

| | | | |
|---|---|---|---|
| 6,249,707 B1* | 6/2001 | Kohnen | A61B 17/3468 607/117 |
| 2006/0069414 A1* | 3/2006 | Imran | A61F 5/0003 607/40 |
| 2008/0200972 A1* | 8/2008 | Rittman | A61B 18/1492 607/117 |
| 2013/0053923 A1* | 2/2013 | Jaax | A61N 1/36146 607/46 |

* cited by examiner

*Primary Examiner* — Ankit D Tejani
(74) *Attorney, Agent, or Firm* — R. Scott Kimsey, Esq.; Klein DeNatale Goldner

(57) ABSTRACT

A neurostimulation lead includes a base, a plurality of electrodes disposed on the base, a steering structure attached to the base, and a guiding wire selectively engageable and disengagable with the steering structure. When the guiding wire is engaged with the steering structure, the guiding wire is operable to move the neurostimulation lead in forward, rearward, side-to-side, and downward directions, without disengaging the steering structure. When the guiding wire is disengaged from the steering structure, the guiding wire can be retracted from the steering structure without disturbing the position of the neurostimulation lead.

10 Claims, 13 Drawing Sheets

SPINAL CORD STIMULATOR PADDLE APPLICATOR, NEUROSTIMULATION LEAD, AND STEERING MECHANISM

RELATED APPLICATIONS

This application claims priority to U.S. patent application Ser. No. 15/087,316, filed Mar. 31, 2016 and entitled Spinal Cord Stimulator Paddle Applicator, Neurostimulation Lead, and Steering Mechanism," which application in turn claims priority from U.S. Provisional Application No. 62/181,546, filed Jun. 18, 2015 and entitled "Spinal Cord Stimulator Paddle Applicator and Method of Use." These applications are incorporated herein by reference in their entirety.

BACKGROUND

1. Field

The present device relates generally to the field of neurostimulation, and more specifically to a device and method for placement of a spinal cord stimulation paddle/lead within the epidural space.

2. Background

Spinal cord stimulation (SCS) is a treatment for patients who experience chronic pain of the back, neck, limbs, or other parts of the body. The treatment typically utilizes wires with leads at the tip, which are inserted into the patient's back near the dorsal spinal column. A pulse generator is inserted subcutaneously, typically in the upper buttock or back of the patient. The pulse generator delivers electrical impulses to the wires, which can induce parathesia in the region of the body where the patient is experiencing pain.

The use of wire leads for SCS has been accompanied by various problems that lead to a reduced effectiveness of pain relief and other complications. For example, the inserted wires may migrate over time so that the electrical impulse supplied by the pulse generator is no longer being applied to the appropriate area of the patient's body. In addition, the wire leads may break or become disconnected. SCS paddles are a type of lead that address some of the problems with the use of wire leads. An SCS paddle typically includes a plurality of electrodes arranged in one or more columns on an underlying paddle structure. The SCS paddle is typically positioned such that the electrodes can address unilateral and bilateral pain. SCS paddles undergo a much lower rate of migration over time as compared to wire leads, and in some instances an SCS paddle may be retained in place by sutures.

SCS paddles do, however, require a surgical procedure for implantation. At least a partial laminectomy is often required to access the epidural space and implant the paddle. The SCS paddle must be maneuvered into place precisely during the surgical procedure.

SUMMARY

The present disclosure provides an applicator for a neurostimulation lead. The applicator includes a base having a first end and second end. The base is configured to receive a neurostimulation lead thereon. A handle extends from the second end of the base of the applicator such that the base can be manipulated while inserting the neurostimulation lead into a patient in need thereof.

The applicator may also include a plurality of fasteners attached to a first surface of the base and defining a space between the fasteners and the base. The nerve stimulation lead may be at least partially received into the spaces defined between the fasteners and the base.

The applicator may also include an elongate bridge extending between the second end of the base and the handle.

The applicator may also include a rigid scoop attached to the first end of the base, the scoop configured to clear a path in the epidural space of a patient during insertion of the neurostimulation lead into the epidural space.

The applicator may also include a locking mechanism associated with the base of the applicator, for securing the lead to the base of the applicator.

The applicator may also include an adjustable stop associated with the base. The adjustable stop may be moveable along the long axis of the applicator. The adjustable stop prevents movement of the neurostimulation lead in the direction of the stop.

The present disclosure also provides a neurostimulation lead having a base with a channel along at least a portion of the length thereof. A plurality of electrodes are disposed along the base. The channel is configured to receive a guiding wire along the length thereof to allow steering of the lead during placement within the body of a patient.

The neurostimulation lead may include a sleeve extending along at least a portion of the channel. The sleeve is configured to receive a guiding wire therethrough.

The neurostimulation lead may also include a stop embedded within the base of the lead at a first end of the channel. The stop prevents the guiding wire from extending therebeyond.

The neurostimulation lead may also include a biasing member embedded within the base of the lead. Such a lead has a first, rolled configuration and a second, unrolled configuration. The biasing member causes transition of the lead from the rolled configuration to the unrolled configuration.

The present disclosure also provides a neurostimulation lead having a base, a plurality of electrodes disposed on the base, and a steering structure associated with the base. The steering structure allows steering of the neurostimulation lead during placement of the lead within the body of a patient.

The steering structure of the neurostimulation lead may include a channel extending along a portion of the length of the base of the lead. The channel may be configured to receive a guiding wire for steering the lead.

The channel of the neurostimulation lead may extend along an exterior surface of the lead.

The channel of the neurostimulation lead may extend through the interior of the lead.

The steering structure of the lead may include a stop configured to engage a guiding wire used to steer the lead.

The steering structure of the lead may include a magnet embedded in the base of the lead.

The steering structure of the lead may include a coil embedded in the base of the lead.

The coil embedded in the base of the lead may be in electrical communication with an implantable pulse generator.

The rolled configuration of a neurostimulation lead may be sufficiently compact to allow percutaneous introduction of the lead into a patient's body.

Another aspect of the present disclosure provides a neurostimulation lead having a base, a plurality of electrodes disposed on the base, a steering structure attached to the base, and a guiding wire selectively engageable and disengagable with the steering structure. When the guiding wire is engaged with the steering structure, the guiding wire is operable to move the neurostimulation lead in forward, rearward, side-to-side, and downward directions, without disengaging the steering structure. When the guiding wire is disengaged from the steering structure, the guiding wire can be retracted from the steering structure without disturbing the position of the neurostimulation lead.

In another aspect of the present disclosure, the guiding wire includes a sheath defining an interior channel along the length of the guiding wire and a retractable locking wire disposed within the sheath. The retractable locking wire is moveable between a first position where the retractable locking wire engages the steering structure and a second position where the retractable locking wire disengages the steering structure. When the locking wire engages the steering structure, the guiding wire is thereby engaged with the steering structure, and when the locking wire disengages the steering structure the guiding wire thereby disengages the steering structure.

In another aspect of the present disclosure, the retractable locking wire has a forked end including a first prong and a second prong.

In another aspect of the present disclosure, the neurostimulation lead includes an actuator at a first end of the guiding wire, the actuator being operable to move the retractable locking wire between the first and second positions.

In another aspect of the present disclosure, the actuator is a shaped portion of the first end of the guiding wire that is capable of manipulation by the user of the neurostimulation lead.

In another aspect of the present disclosure, the guiding wire includes a sheath defining an interior channel along the length of the guiding wire and a tube disposed within the channel and extending along the length of the channel. The tube has a first end having a bladder in pneumatic communication with the tube. The bladder is selectively inflatable and deflatable, and when the bladder is in the inflated state the external surface of the bladder engages the steering mechanism, thereby engaging the guiding wire with the steering mechanism. When the bladder is in the deflated state the bladder disengages the steering structure, thereby disengaging the guiding wire from the steering structure.

In another aspect of the present disclosure, the inflation/deflation mechanism is provided in pneumatic communication with the second end of the tube.

In another aspect of the present disclosure, the inflation/deflation mechanism is a bulb with a valve. The bulb and valve are operable for selective inflation and deflation of the bladder.

In another aspect of the present disclosure, the inflation/deflation mechanism is an electrical pump.

In another aspect of the present disclosure, the guiding wire has an electromagnet at a first end thereof, and the steering structure includes a magnetic material. The electromagnet is selectively energizable and de-energizable. When the electromagnet is in the energized state it engages the steering structure, thereby engaging the guiding wire with the steering structure. When the electromagnet is in the de-energized state, it disengages the steering structure, thereby disengaging the guiding wire from the steering structure.

In another aspect of the present disclosure includes a power source in electrical communication with the electromagnet. The power source is operable by a user of the neurostimulation lead to selective energize and de-energize the electromagnet.

Another aspect of the present disclosure includes a base, a plurality of electrodes disposed on the base, and a steering structure attached to the base. The base defines a channel along at least a portion of the length of the base. The channel is configured to receive a guiding wire that is selectively engageable and disengageable with the steering structure.

In another aspect of the present disclosure, the neurostimulation lead includes a sleeve extending along at least a portion of the length of the channel. The guiding wire is configured to extend through the sleeve.

In another aspect of the present disclosure, the guiding wire includes a forked end having a first prong and a second prong. The first and second prongs of the guiding wire engage and disengage the steering structure.

DETAILED DESCRIPTION

Figure 1:
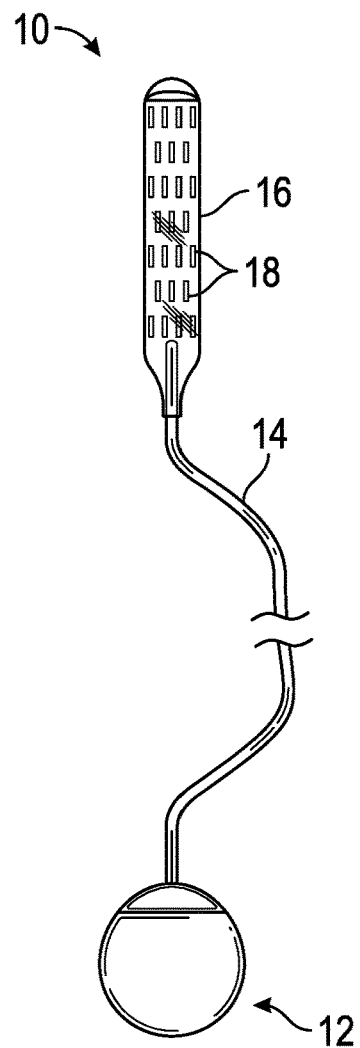
FIG. 1 depicts a prior art SCS paddle/lead system.

Various embodiments of the devices, methods, and systems of the present disclosure are provided herein, and include numerous specific details that are set forth to provide a thorough understanding of the structure, function, and use of the embodiments. It should be noted that in some instances well-known operations, components, and elements of the embodiments described herein may be provided with less detail. Those of ordinary skill in the art will understand such operations, components, and elements of the embodiments described herein upon reading this disclosure. Further, those of ordinary skill in the art will recognize that the embodiments described herein and shown in the accompanying drawings are non-limiting, and that the structural and functional details provided herein may be exemplary only and do not limit the scope of the present embodiments.

Throughout this disclosure, phrases such as "one embodiment," "some embodiments," "various embodiments," "an embodiment," "an exemplary embodiment," or similar terminology may be used. It is to be understood that such language means that the particular structure, feature, step, element, or the like of characteristics described is included in at least one embodiment. Such phrases, then, do not necessarily all refer to the same embodiment, and the particular structures, features, steps, elements, and the like described herein may be combined in any suitable manner in one or more embodiments.

The terms "forward" and "rearward" are used herein with respect to the SCS paddles/leads described. For purposes of this disclosure, the "rearward" end of the lead is that end to which the extension wire is attached, while the forward end of the lead is that end of the lead opposite the rearward end. Further, the terms "upward," "downward," "top," or "bottom" may be used herein. For purposes of this disclosure, the "top" of the neurostimulation lead is that surface facing the viewing in FIGS. 3, 4, 14, and 17, for example. Such terms are used for clarity and are not intended to limit the scope of the present disclosure except as clearly indicated in the claims appended hereto. The use of such terms is not intended to imply any given orientation of the present device during use.

Turning to the drawings, wherein like numerals indicate like parts, the numeral 10 refers generally to a Spinal Cord Stimulation (SCS) system known in the art. SCS system 10, shown in FIG. 1, includes an Implantable Pulse generator (IPG) 12, an extension wire 14, and a lead 16 (also referred to herein as a "paddle" or a "neurostimulation lead"). The IPG is a neurostimulator that generates a mild electrical current. This current passes along extension wire 14 to lead 16, where the current is delivered to the nerve fibers of the spinal column. The electrical current induces action potentials in large-diameter nerve fibers of the spinal column. An action potential in these nerve fibers blocks action potentials in small-diameter nerve fibers of the spinal column, and it is the small-diameter nerve fibers that transmit pain information. Thus, the use of the SCS system to generate action potentials in large-diameter nerve fibers effectively blocks neuropathic pain by inducing parathesia at the area affected by lead 16. It is contemplated that the various embodiments of the present disclosure may be used therapeutically on the spinal cord of a patient, or may be used along various nerves of the patient's body.

Lead 16 shown in FIG. 1 is a paddle-style lead having a plurality of electrodes 18 arrayed along the length and width of the lead. Lead 16 is preferably constructed of a physiologically inert plastic and provided as a thin, flexible strip of material. IPG 12 may be programmed to provide electrical current to specific electrodes 18 in the array, based on the location of tissue needing stimulation. The amount and frequency of current directed to individual electrodes 18 may be utilized to create a pattern of directed stimulation by a physician. Typically, some of the electrodes are programmed to act as anodes, others as cathodes, and others may be left "off." A variety of complex stimulation patterns may by programmed by the physician.

Surgical implantation of SCS system 10 generally begins with placement of one or more leads 16. Placement of a lead 16 may be accomplished with the aid of fluoroscopy. The surgeon makes an incision in the patient's back at the site of placement of lead 16. This incision exposes the bony arch of the vertebra beneath the skin. A portion of the lamina (the back part of the vertebra that covers the spinal canal) is removed via a procedure known as a laminectomy. One or more leads 16 is placed in the epidural space above the spinal canal and secured using sutures.

With lead 16 in place, extension wire 14 is threaded beneath the skin to the abdomen or buttock, where IPG 12 will be located. IPG 12 is generally implanted beneath the skin of a patient in a pocket created by the surgeon between the dermal and muscle layers of the patient's body. Extension wire 14 is attached to IPG 12, and IPG 12 is sutured to the thick fascia layer overlaying the muscles.

Figure 2:
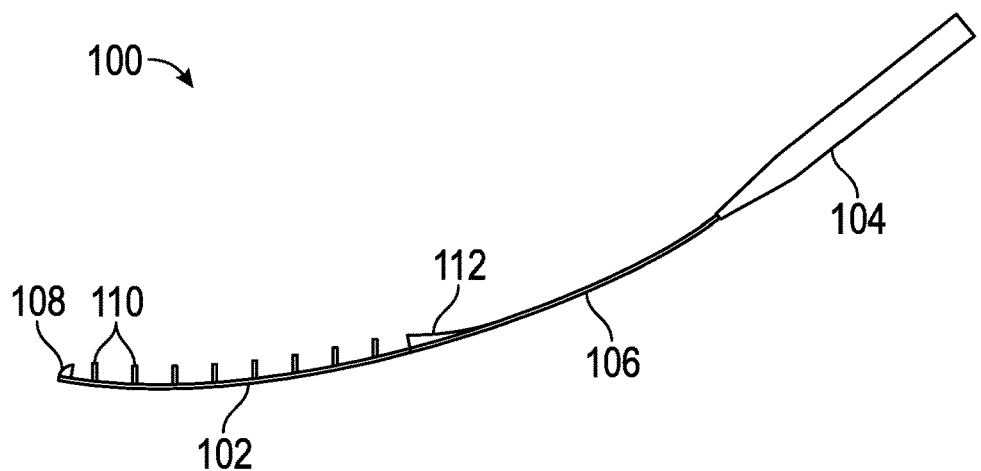
FIG. 2 is a side view of one embodiment of a lead applicator of the present disclosure.

One aspect of the present disclosure is directed to a spinal cord stimulator (SCS) paddle applicator 100, shown in FIG. 2. Applicator 100 is used to properly position an SCS paddle, or lead, 16, described above, within the epidural space of a patient. Applicator 100 includes a base 102 on which the lead is received. A plurality of fasteners 110 disposed along the surface of base 102 are provided to hold the lead in place. Fasteners 110 are preferably formed structures of physiologically inert plastic that provide sufficient space between and upper portion of each fastener 110 and base 102 to receive the lead therebetween. Applicator 100 also includes a handle 104 to allow for manipulation of applicator 100. A bridge 106 extends between handle 104 and base 102.

The front end of applicator 100 preferably includes a thick, dull-edged portion of material 108, which may be referred to herein as a "scoop." It should be noted that the use of the term "scoop" does not imply any functional or structural limitations to this feature of applicator 100, but merely provides an appropriate term to use as a point of reference herein. The structure and function of scoop 108 should be construed broadly in accordance with this disclosure. Scoop 108 has sufficient rigidity to clear out scar tissue or other debris in the epidural space, thereby forming a path therethrough for insertion of the SCS paddle. Any suitable structure or shape of scoop 108 may be utilized in order to provide applicator 100 with the ability to clear a path through the epidural space. In still other embodiments, only a portion of the applicator, such as, for example, scoop 108, may be constructed of radio-opaque materials.

The applicator should be constructed of a semi-rigid, radio-opaque material. Various such materials are known in the art. Such materials allow use of the device, and placement of the lead, under fluoroscopic guidance. In other embodiments of the present disclosure, however, the lead may be provided with RFID or other tags such that the position and maneuvering of the lead may be directed electronically.

In use, a lead such as lead 16 is positioned on the flat base 102 of applicator 100. The lead is positioned between the scoop 108 and bridge 106, and may be located at various places along base 102. In embodiments of applicator 100 that include attachments 110, the lead is contained between attachments 110 and base 102 of applicator 100. Some embodiments of applicator 100 further include an adjustable stop 112 located at the rearward end of base 102, just before bridge 106. Adjustable stop 112 prevents the lead contained on applicator 100 from being displaced rearward on applicator 100 during the insertion process. Stop 112 is preferably adjustably positionable at various points along the rear portion of base 102 so that the precise position of the lead on base 102 may be varied and stop 112 still used to maintain the lead in the proper position.

Figure 3:
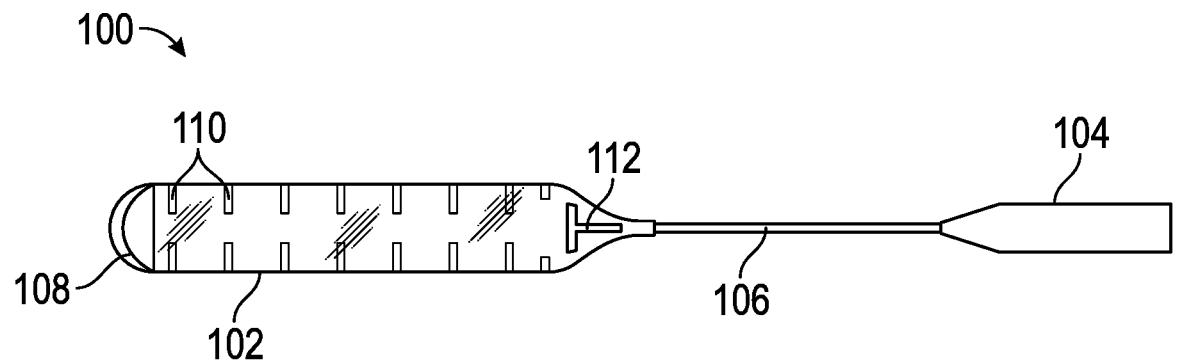
FIG. 3 is a top view of the embodiment of a lead applicator shown in FIG. 2.

FIG. 3 provides a top view of the embodiment of an applicator 100 depicted in FIG. 2. Shown in the figure are base 102, handle 104, and bridge 106 extending between the handle and the base. Some embodiments of applicator 100 may include only a base 102 and handle 104 attached thereto, with no bridge 106 extending therebetween. Attachments 110 can also be seen extending along the length of base 102. Adjustable stop 112 is shown in one of many possible positions available to hold a lead in place on base 102.

In the embodiments of applicator 100 shown in the drawings, attachments 110 are shown distributed across an upper surface of base 102. It is contemplated, however, that some embodiments of applicator 100 may include attachments 110 across the lower surface thereof, in place of, or in addition to, the attachments 110 extending across the upper surface of base 102. Placement of attachments 110 along the bottom surface of base 102 allows a user of applicator 100 to affix a lead to the bottom of base 102, which may, in certain cases, allow a more desirable placement of the lead than disposing the lead on the top of base 102.

Adjustable stop 112 may be any suitable adjustable mechanism that, when in a first position, allows a lead to be inserted onto base 102 of applicator 100 and, in a second position, holds the lead firmly in place so that the lead does not become dislodged from applicator 100 during placement of the lead at the proper point along the spine of a patient. Adjustable stop 112 may include, for example, a stop body moveable along a channel. The channel may include inward-projecting tabs or other structures configured to hold the stop body in place. Depressing the stop body may disengage the stop body from the inward-projecting tabs, thereby allowing free motion of the stop body within the channel. When the stop body is released, the inward-projecting tabs again engage the stop body and prevent movement thereof. When a lead is to be inserted onto base 102, the stop body is depressed and moved along the channel to allow sufficient room for the lead to be placed on base 102. Once the lead is properly positioned on base 102, the stop body is again depressed and moved, this time in a forward direction until the stop body engages the lead sufficiently to hold it in place. The above is simply an exemplary mechanism for employing a moveable, adjustable stop with the applicator of the present disclosure. It is contemplated that any suitable structure or method may be utilized.

Although a tab and channel embodiment of adjustable stop 112 is described above, it is contemplated that any suitable adjustable stop mechanism may be used, including, but not limited to, mechanisms that are adjustable via the action of one or more wires, and mechanisms that are adjustable via a spring and detent pin, wherein depression of the detent pin allows movement of the stop body and releasing the detent pin allows the stop body to be secured in place. Control of the adjustable stop may take place at the handle of applicator 100, rather than directly at the point of the adjustable stop.

Figure 4:
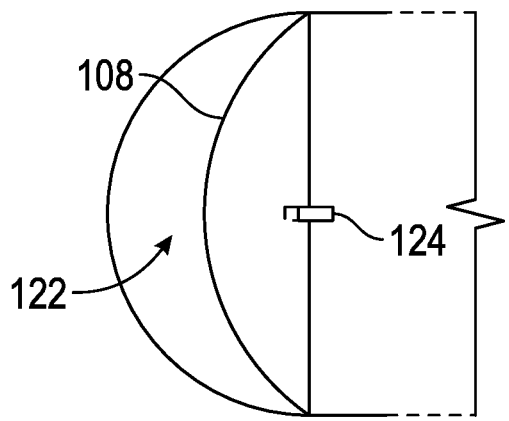
FIG. 4 is a top view of a portion of an embodiment of a lead applicator having a locking and release mechanism associated therewith.

Some embodiments of applicator 100 may include a locking and release mechanism 122, such as that shown in FIG. 4, at or near the forward end of applicator 100. In some embodiments, for example, the locking and release mechanism may be associated with the rearward portion of scoop 108. Such a mechanism allows the lead to be maneuvered into place, including pushing, pulling, or sideways movement of applicator 100, without the lead being detached from the applicator 100 prematurely. The locking and release mechanism prevents more than just the rearward motion of the lead prevented by adjustable stop 112, and may be used in combination with, or without, an adjustable stop. In embodiments of applicator 100 having a locking and releasing mechanism, once the lead is properly positioned the mechanism may be actuated to release the lead.

Figure 5:
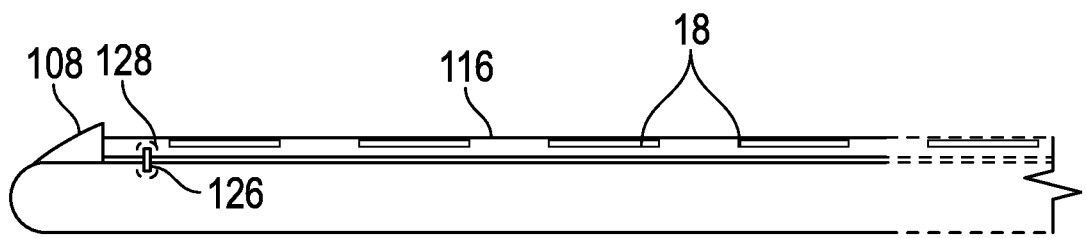
FIG. 5 is a side view of a portion of an alternative embodiment of a lead applicator having a locking and release mechanism associated therewith.

The embodiment of locking and release mechanism 122 shown in FIG. 4 includes a retractable detent pin 124 that emerges from an opening in a rearward portion of scoop 108. In such embodiments, detent pin 124 may simply extend over a portion of the lead, thereby holding the lead in place. In other embodiments of applicator 100, such as that shown in FIG. 5, a detent pin 126 may emerge from base 102 to engage a corresponding opening 128 defined in the lead disposed on base 102. In either of the above-identified embodiments, a wire control mechanism may be used to retract and release the detent pin. It is contemplated that any suitable method of controlling the engagement and disengagement of the detent pin may be used.

Figure 6A:
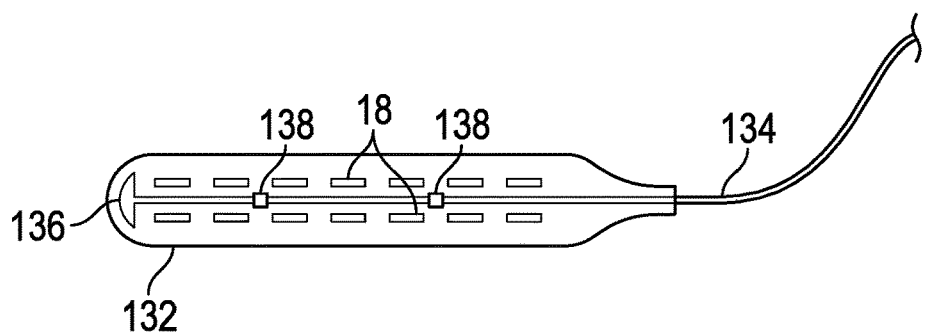
FIG. 6A is a top view of one embodiment of a wire-guided lead of the present disclosure.
Figure 6B:
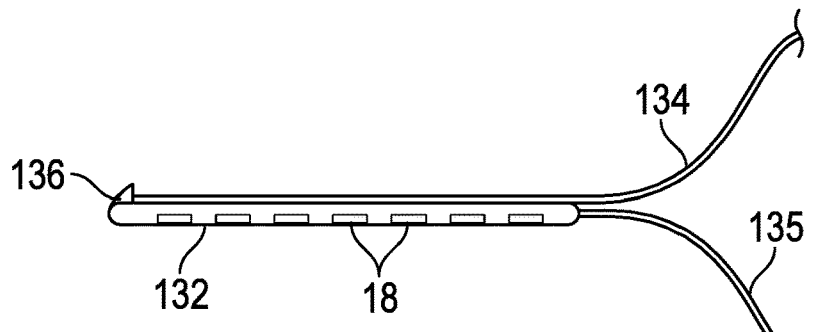
FIG. 6B is a side view of the embodiment of a wire-guided lead of FIG. 6A.

While an applicator 100, such as shown in FIGS. 1 through 5 and described above, may be used to steer the lead and place it in its proper position, it is contemplated that a guiding wire 134 may also be used to steer a lead 132, as depicted in FIGS. 6A and 6B. Guiding wire 134 is preferably a firm wire that engages lead 132 and allows for the steering of lead 132 within the epidural space. Guiding wire 134 is wholly removed from the patient's body after use and is not associated with lead 132 during normal, daily use of the lead. If it becomes necessary to reposition the lead as a result of unwanted migration, the lead may be accessed surgically and guiding wire 134 reinserted into lead 132 in order to reposition the lead.

As shown in FIGS. 6A 6B, lead 132 preferably includes a steering structure such as hood 136 at a forward end thereof. Hood 136 is configured to receive an end of guiding wire 134 such that guiding wire 134 can be used to steer lead 132. It is preferred that guiding wire 134 engage hood 136 in a releasable, locking manner so that lead 132 can be positioned in various directions, including rearward, without guiding wire 134 inadvertently disengaging lead 132. The distal end of guiding wire 134 may, for example, include an actuator mechanism that actuates a locking mechanism such as a pin, bladder, or other structure at the proximal end (i.e. the end engaging hood 136) of guiding wire 134. Alternatively, hood 136 may include structure configured to engage or disengage guiding wire 134. Attachments 138, such as clips, sleeves, or the like, may optionally be provided along the length of lead 132 such that guiding wire 134 may releasably engage lead 132 along its length. This may provide for greater stability and control of lead 132 during the positioning process. Hood 136 may be constructed of any suitable material, however it is preferred that hood 136 be constructed of a radio-opaque material or other materials that allows the position of hood 138 to be imaged during insertion or positioning of lead 132.

It is contemplated that various embodiments of the present disclosure may allow for different levels of movement or positioning of a lead described herein. For example, leads with structure to lock a guiding wire may be moved forward, backward, and side to side. Other leads, lacking such a locking structure, may allow forward and side to side adjustment of the lead, but disengage the lead from the guiding wire when the guiding wire is pulled in a rearward direction.

Figure 7:
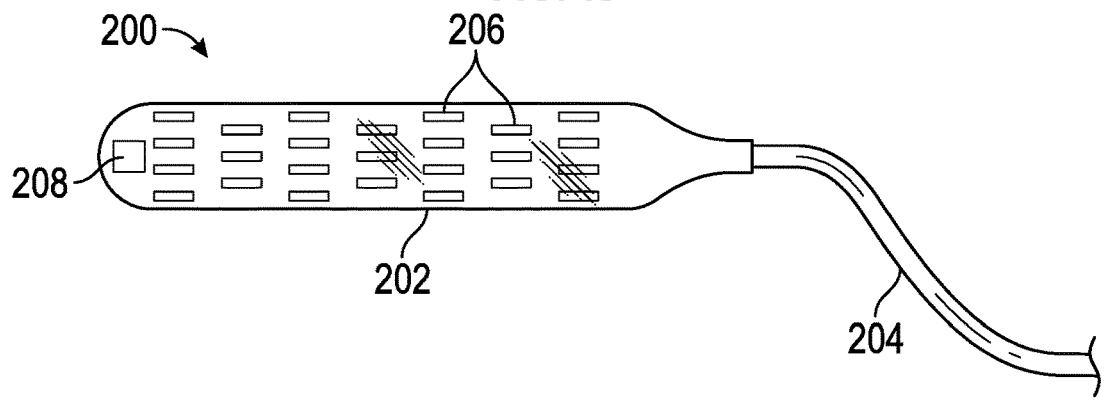
FIG. 7 is a top view of one embodiment of a lead of the present disclosure having a magnetic element associated therewith.

Other embodiments of the present disclosure include leads that incorporate a magnetic element for steering the lead within a patient's body. The magnetic element may be used for initial placement of the lead, or for corrective placement of the lead after unwanted migration. One example of such a lead is lead 200, shown in FIG. 7.

Lead 200 includes many components that have been described above with respect to other embodiments disclosed herein, including extension wire 204 (which communicates with an IPG, not shown), a body 202, and a plurality of electrodes 206 disposed on the body 202. Lead 200 also includes a magnetic element 208, preferably positioned at the forward end of lead 200. As used herein, the term "magnetic element" may include a magnetic material, or may include a structure, such as a coil, via which a magnetic field may be generated.

In embodiments of lead 200 wherein magnetic element 208 includes magnetic material, it is preferred that strong magnetic materials are used. Examples of strong magnetic materials include rare earth magnets, such as neodymium-iron-boron and samarium-cobalt materials. It is contemplated, however, that any suitable magnetic material, including ferromagnetic materials, may be used. It is preferred that magnetic element 208 be coated, both to protect the magnetic material from the environment of the body, and to ensure that magnetic element 208 is physiologically inert. It is contemplated that magnetic element 208 may be dipped in silicone prior to incorporation into lead 200, or may be coated with silicone via an injection molding process. Physiologically inert metal coatings, such as nickel and cobalt, may also be used. Any suitable coating material may be used with magnetic element 208.

In some embodiments of lead 200, magnetic element 208 may include magnetic nanoparticles, such as ferrite or iron oxide nanoparticles. Such nanoparticles may be provided with a silica coating to ensure that the magnetic nanoparticles are suitably inert. In other embodiments, the magnetic nanoparticles may include a gold coating. Any suitable coating may be used with respect to the nanoparticles.

Figure 8:
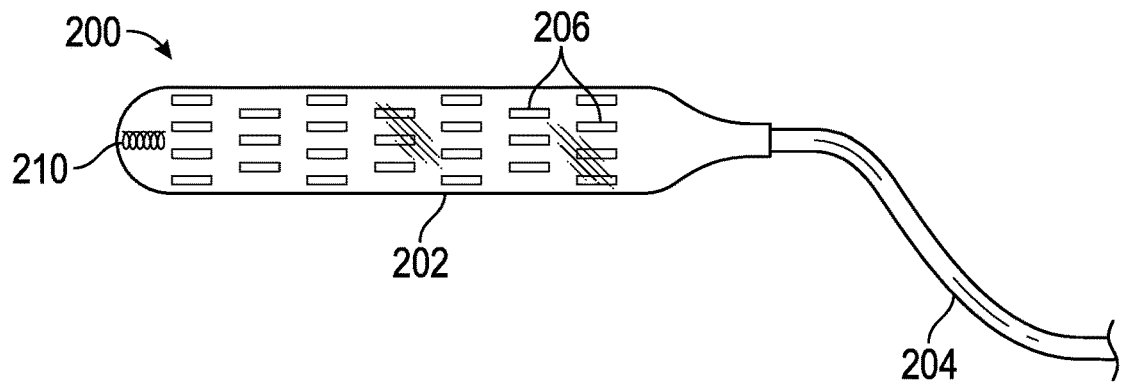
FIG. 8 is a top view of one embodiment of a lead of the present disclosure having a coil associated therewith.

FIG. 8 depicts an alternative embodiment of lead 200 having a coil 210 associated therewith. It is contemplated that coil 210 may be energized by current from an IPG (not shown) when it is necessary to adjust the position of lead 200. Energizing the coil in this manner provides a magnetic moment proportional to the product of the number of turns in the coil, the current passing through the coil, and the cross-sectional area of the coil wire. Those of skill in the art will be able, upon reading this disclosure, to devise a suitable coil for use with lead 200, and to program the IPG to provide a suitable current to the coil in order to steer lead 200. By way of example, in a lead 200 having a thickness of 2.0 mm, a coil of AWG #50 magnet wire may be used. The coil may be wound with one-thousand turns. The wire has a diameter of 0.025 mm, and would result in a coil 210 having a length of 5 mm and a total thickness of 0.125 mm. The coil 210 could be embedded in the body 202 of lead 200. When 0.1 amps of current are applied to the exemplary coil 210 described above, a magnetic moment of 0.4 nanoTesla cubic meters results. This is approximately 1/10 the magnetic moment of an equivalently-sized rare-earth neodymium-iron-boron magnet. Thus, the external magnetic field (see below) would have to be about ten times the magnetic field required for a similarly-sized rare-earth permanent magnet. Although coil 210 is shown in the drawings as being positioned at the forward end of lead 200, it is contemplated that coil 210 may be positioned at any suitable location on lead 200, or that multiple coils 210 may be utilized, with a coil 210 positioned, for example, along one side of lead 210, while another coil is positioned along the other side of lead 210. Such embodiments may also include the coil 210 at the forward end of lead 200.

Steering of lead 200 may be accomplished using a permanent magnet held outside of the body, the motion of the magnet outside of the body causing a corresponding motion of lead 200 within the body of a patient. A variety of permanent magnets are known in the art, and it is contemplated that any suitable permanent magnet may be used to steer lead 200. Alternatively, a magnetic field may be generated in the operative region of the patient's body by external electromagnets, permanent magnets, or superconducting electromagnets affixed to an external structure. In embodiments of lead 200 using one or more coils 210, the coils may be energized in their entirety, or selectively energized to create a local magnetic moment at the forward end of lead 200. This local magnetic moment responds to the externally-produced magnetic field, causing lead 200 to move relative to the magnetic field.

As noted above, steering of lead 200 may be accomplished manually, such as by a physician wielding a magnet or an instrument having a magnet associated therewith and directing the movement of the lead by moving the magnet or instrument. It is contemplated, however, the external structures having permanent magnets, electromagnets, superconducting electromagnets, or the like, may be computer-controlled to allow for fine tuning of the steering of lead 200. Computer control of a magnetic field to which lead 200 responds may be pre-programmed, based on a physician's assessment of the location of lead 200 and the adjustments necessary, or may be provided in real time, with lead 200 responding to instructions of the physician while movement of the lead is monitored via fluoroscopy or other suitable methods.

Figure 9:
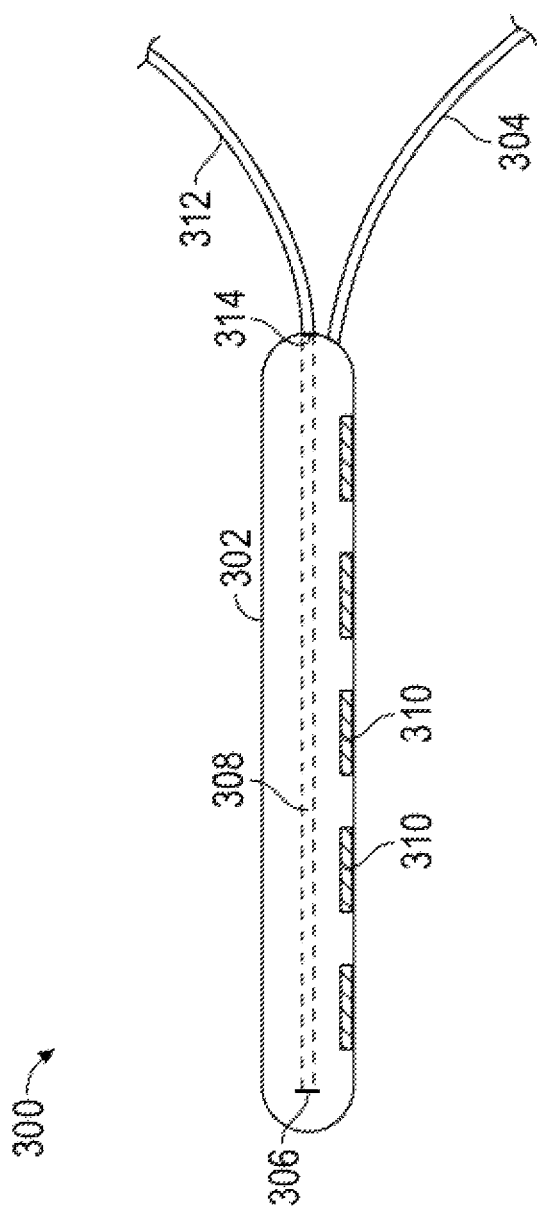
FIG. 9 is a side view of one embodiment of a lead of the present disclosure having an internal channel for receipt of a guiding wire therein.

FIG. 9 depicts one embodiment of a lead 300 of the present disclosure having a channel 308 formed through a portion of the interior of the body thereof. Guiding wire 312 is inserted through an opening 314 and along internal channel 308 until the end of guiding wire 312 encounters stop 306. Stop 306 can be a structure separate from the body of the lead and embedded therein, or may simply be the end of channel 308. Guiding wire 312, being inserted into internal channel 308 of lead 302, can then be used to steer or adjust the position of lead 302 such that electrodes 310 are properly positioned.

Figure 10:
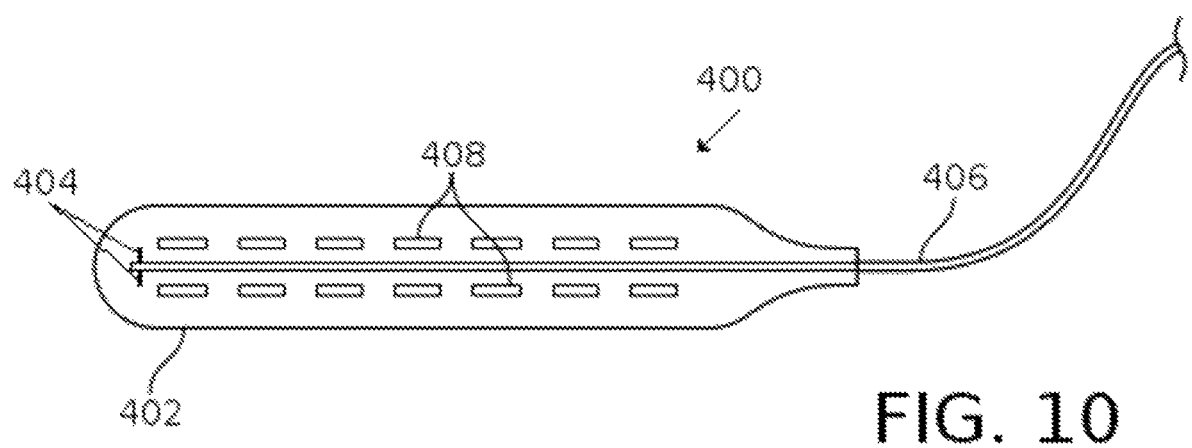
FIG. 10 is a top view of one embodiment of a lead of the present disclosure having a radio-opaque marker associated therewith.

FIG. 10 depicts one embodiment of a lead 400 of the present disclosure having a radio-opaque marker associated therewith. Lead 400 may be configured to utilize a guiding wire 406 that is secured to the surface of lead 400, or may be configured to utilize a guiding wire 406 that is received internally into a channel within lead 406. Lead 400 includes markers 404 that are radio-opaque or otherwise visible during imaging of a procedure to steer or guide lead 400 so that electrodes 408 are properly positioned. Guiding wire 406 is also visible via imaging, and lead 400 is configured so that when guiding wire 406 is properly positioned thereon, the end of guiding wire 406 forms a "+" or cross-like structure with markers 404 so that the fact that guiding wire 406 is properly positioned can be seen via imaging. When guiding wire 406 is not properly positioned, a partial or complete gap may be visible between markers 404.

Figure 11:
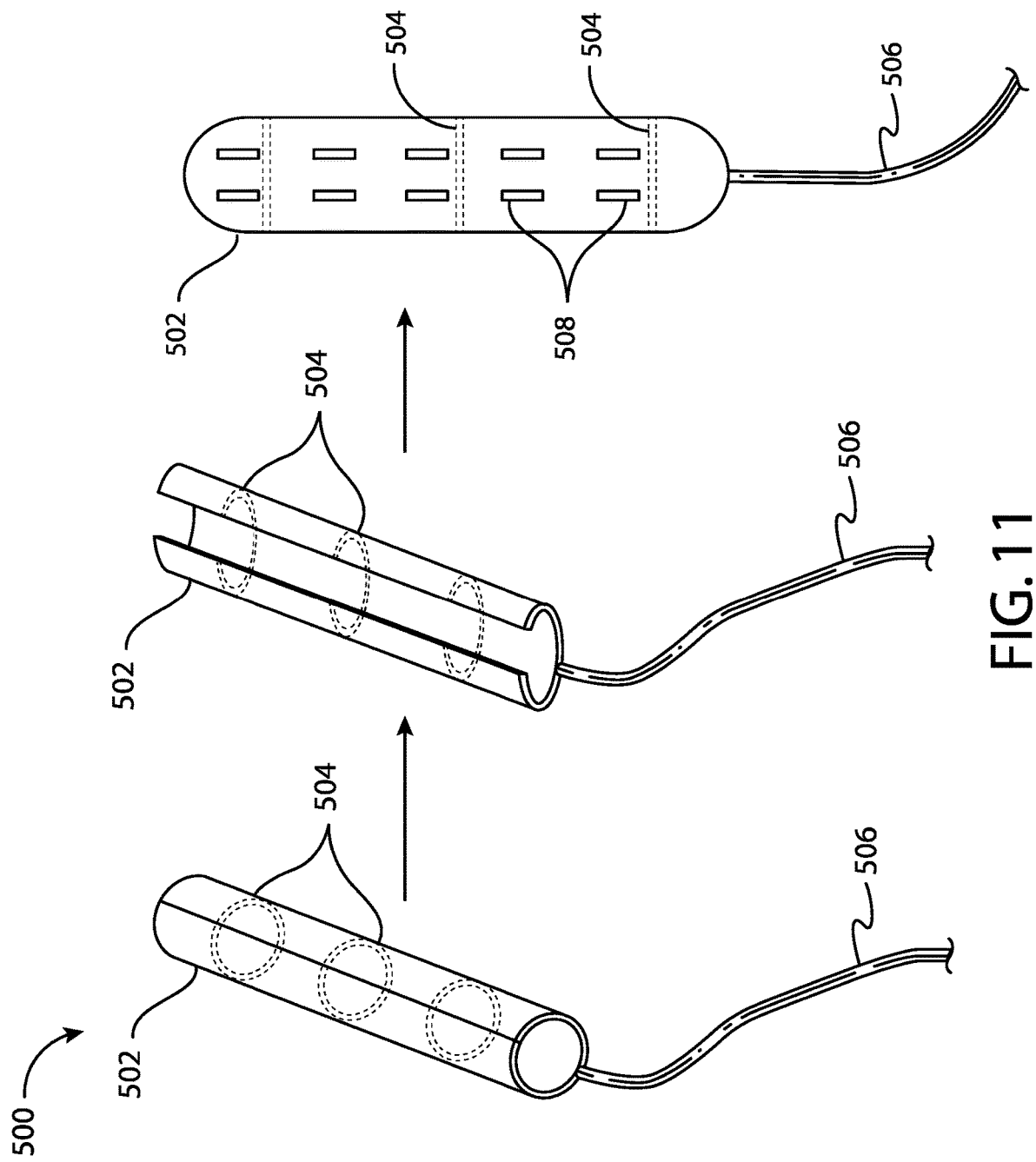
FIG. 11 is a perspective view of an embodiment lead of the present disclosure depicting the lead transitioning from a rolled to an unrolled state.

FIG. 11 depicts an alternate embodiment of a lead 500 of the present disclosure. Lead 500 is configured to be inserted into a patient using a less invasive procedure than the aforementioned embodiments of the leads of the present disclosure.

As shown in FIG. 11, lead 500 has a rolled configuration, and it is preferably in this configuration that lead 500 is inserted into the body of a patient. It is preferred that lead 500 be rolled into a sufficiently tight configuration that lead 500 can be introduced into a patient's body percutaneously. This is also preferred for the other rolled lead embodiments described in this disclosure. Body 502 of lead 500 includes a plurality of wires 504 embedded therein. Wires 504 are flexible, but retain memory of their straight configurations and have a tendency to return to those configurations. Once lead 500 has been placed within the body of a patient and positioned properly, lead 500 is allowed to unroll, as shown in FIG. 11. Lead 500 unrolls to the final configuration shown in FIG. 11, wherein lead 500 has substantially the same shape as the aforementioned embodiments of leads of the present disclosure. Once properly positioned and unrolled, lead 500 performs pain treatment functions with respect to one or more nerves or the spinal cord as described with respect to other embodiments, above. It is contemplated that the various features of other embodiments of the present disclosure described above may also be used in conjunction with lead 500, or with other embodiments of the present leads described below.

Figure 12:
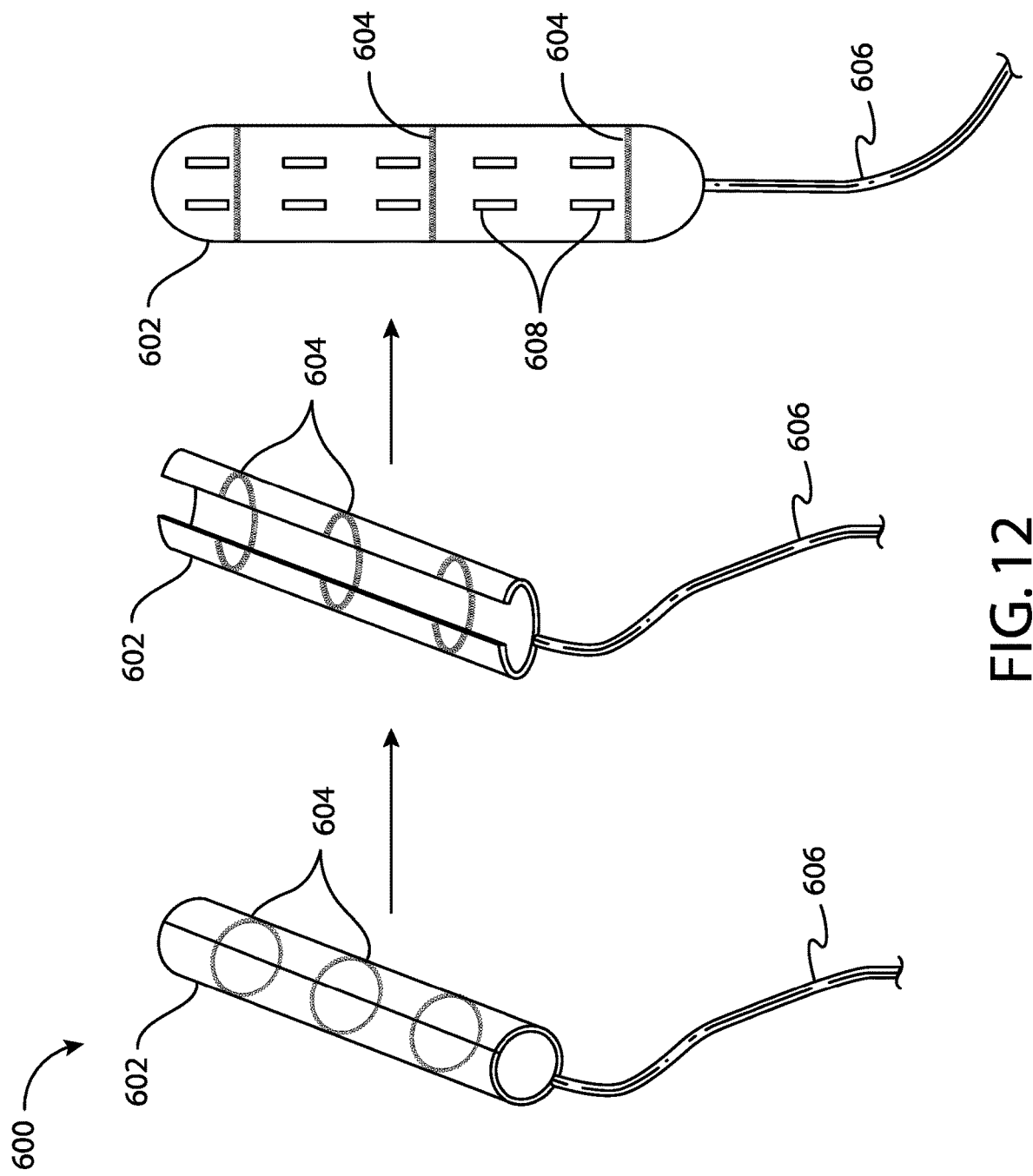
FIG. 12 is a perspective view of another embodiment of a lead of the present disclosure depicting the lead transitioning from a rolled to an unrolled state.

FIG. 12 depicts an embodiment of a lead 600 of the present disclosure. Lead 600 operates in much the same manner as lead 500, described above, however springs 604 are used in place of wires 504, embedded within body 602 to bias the body of lead 600 into an unrolled configuration once lead 600 has been properly placed within the body of a patient.

Figure 13:
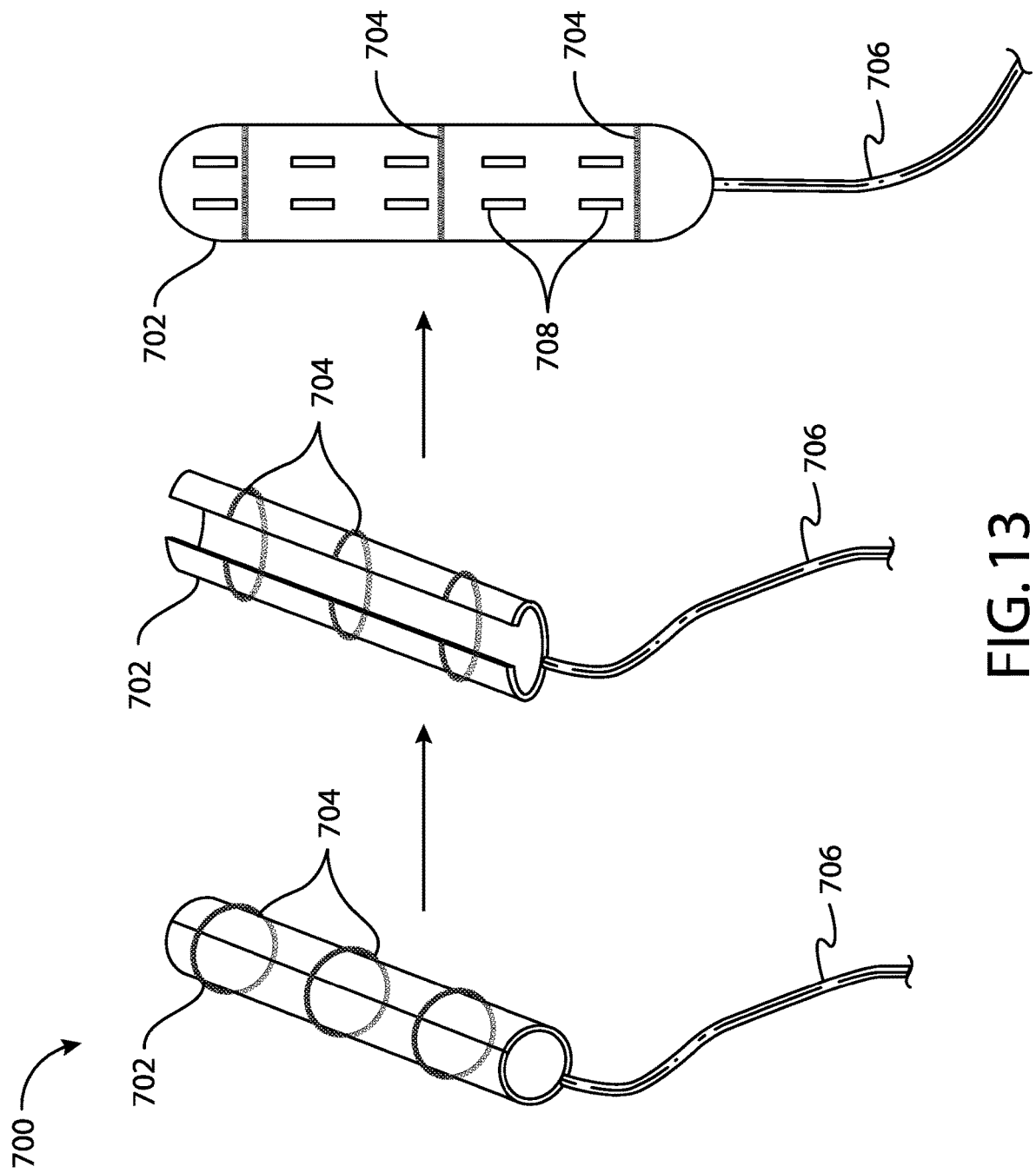
FIG. 13 is a perspective view of yet another embodiment of a lead of the present disclosure depicting the lead transitioning from a rolled to an unrolled state.

FIG. 13 depicts an embodiment of a lead 700 of the present disclosure that is delivered to the proper location in a patient in a rolled form, as with leads 500 and 600. Lead 700 includes springs 704 on an exterior surface thereof. The ends of spring 704 are preferentially embedded in body 702 of lead 700, though any suitable attachment mechanism may be used. When lead 700 is in the rolled configuration, springs 704 are distended and have a tendency to resume their wound shape. When lead 700 is properly placed within the body of a patient, it is allowed to unroll and springs 704 resume their normal shape, causing lead 700 to unroll as they move from a distended to non-distended form.

Rolled embodiments of leads of the present disclosure, such as those described above, may be delivered to the desired site within a patient by any suitable means, including via the use of a needle or a catheter. In embodiments utilizing a catheter for placement, for example, a catheter and pusher may be used to deliver the lead. The catheter may be initially guided to the desired site using guide wires, which may be visible using one of various imaging technologies so precise placement of the catheter can be achieved. The guide wires may then be removed and the rolled lead inserted into the lumen of the catheter. A "pusher," which may be, for example, a wire having a distal end configured to push the roller lead along the length of the catheter, may then be used, the pusher advancing the rolled lead through the lumen of the catheter as the pusher is advanced therethrough. When the rolled lead reaches the end of the catheter, which is positioned at the desired location for introduction of the lead into the patient's body, the pusher advances the lead out of the lumen of the catheter and into the proper position.

In some embodiments of the present disclosure, a more precise control and placement of the rolled lead via the pusher may be achieved by binding the pusher, metal to metal, with a guide structure on the rolled lead. The pusher and the guide structure may be constructed from dissimilar materials, such that when low electrical current is passed through the pusher and the guide structure, the link between the pusher and the guide structure is severed by electrolysis and the pusher can be retracted without disturbing the position of the lead. Further, rolled leads may utilize other structures disclosed herein, such as structures that allow for the use of a guiding wire to properly place the lead.

Various coils, springs, or shape-remembering wires described herein may be constructed of any suitable material. It is preferred that in embodiments wherein such structures are exposed to the patient's body they be constructed of biocompatible metals or other biocompatible materials. The coils, springs, or other structures may be constructed of radiopaque materials, or other materials that allow visualization via imaging, or may have associated therewith such materials (such as, for example, radiopaque polymers or fibers).

Figure 14:
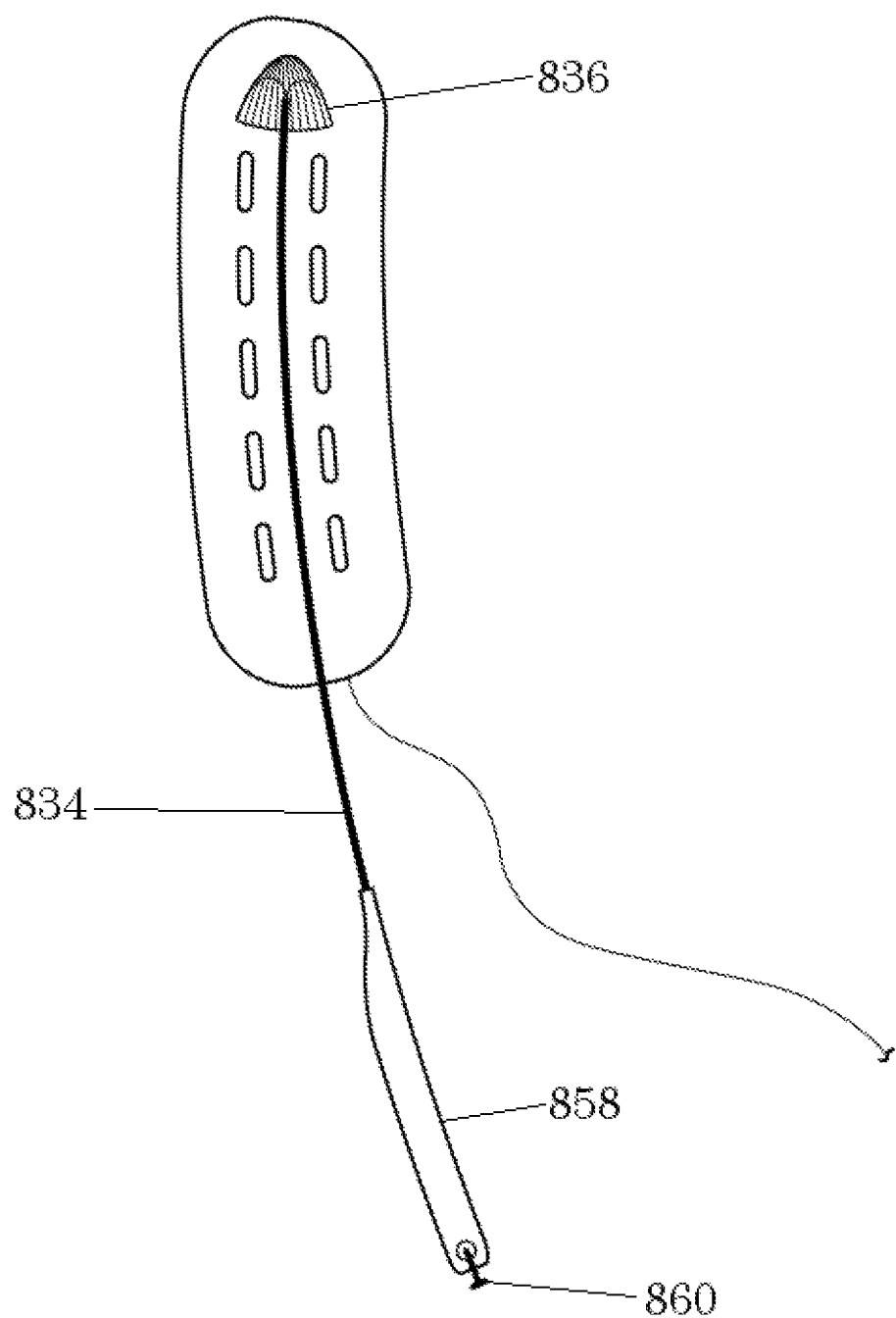
FIG. 14 is a top view of an SCS paddle incorporating one embodiment of a locking mechanism of the present disclosure.

FIG. 14 provides a top view of an SCS paddle lead 832 having one embodiment of a locking mechanism associated therewith. The locking mechanism depicted allows guiding wire 834 to selectively engage and disengage a steering structure such as hood 836. When guiding wire 834 is engaged with hood 836, a user may move SCS paddle lead 832 in forward, sideways, and rearward motions without guiding wire 834 disengaging hood 836, which would cause the user to lose the ability to position SCS paddle lead 832. Once SCS paddle lead 832 is positioned as necessary or desired by the user, guiding wire 834 may be disengaged from hood 836 and guiding wire 834 may be removed without disturbing the placement of SCS paddle lead 832.

In the embodiment shown in FIG. 14, guiding wire 834 preferably includes a sheath 850 with a retractable locking wire 852 contained therein. Retractable locking wire 852 preferably includes a forked end having first and second prongs 854 and 856, respectively, at that end of retractable locking wire 852. First prong 854 and second prong 856 are configured to engage the interior of hood 836 in a locking manner.

It is contemplated that first prong 854 and second prong 856 of retractable locking wire 852 may engage with openings, formations, or other physical structures on the interior surface of hood 836 designed specifically for that purpose, or that they may simply engaged with a smooth interior surface of hood 836. Further, although retractable locking wire 852 is shown in the figures as disposed within a sheath 850 that protects retractable locking wire 852 and facilitates smoother movement thereof, it is contemplated that in some embodiments the sheath may be eliminated.

Control of the retractable locking wire, that is, the engagement and disengagement thereof with respect to hood 836, may be accomplished in any suitable manner. For example, an actuator 860 may be provided at the end of the device being manipulated by a user during a surgical procedure. Actuator 860 may operate by a purely mechanical mechanism, such as in embodiments where a user forces actuator 860 inward and thereby pushes first and second prongs 854 and 856 outward and away from sheath 850, causing the prongs to engage the interior surface of hood 836. In such embodiments, simply releasing actuator 860 may be sufficient to disengage first and second prongs 854 and 856, though it is contemplated that in other such embodiments it may be necessary to physically retract actuator 860 in order to disengage the prongs from hood 836.

In the embodiment shown in FIG. 14, the device includes a handle 858 to allow a user to better manipulate the device, as well as the locking mechanism thereof. It is contemplated that in some embodiments, however, such a handle may be eliminated.

Although the embodiment of the present device described above utilizes a purely mechanical mechanism for engaging and disengaging the locking mechanism, it is contemplated that electrical means of engaging and disengaging the locking mechanism may also be provided. Such electrical means may draw power from the power source dedicated to the SCS paddle, or from an external power source used during surgery.

Figure 15:
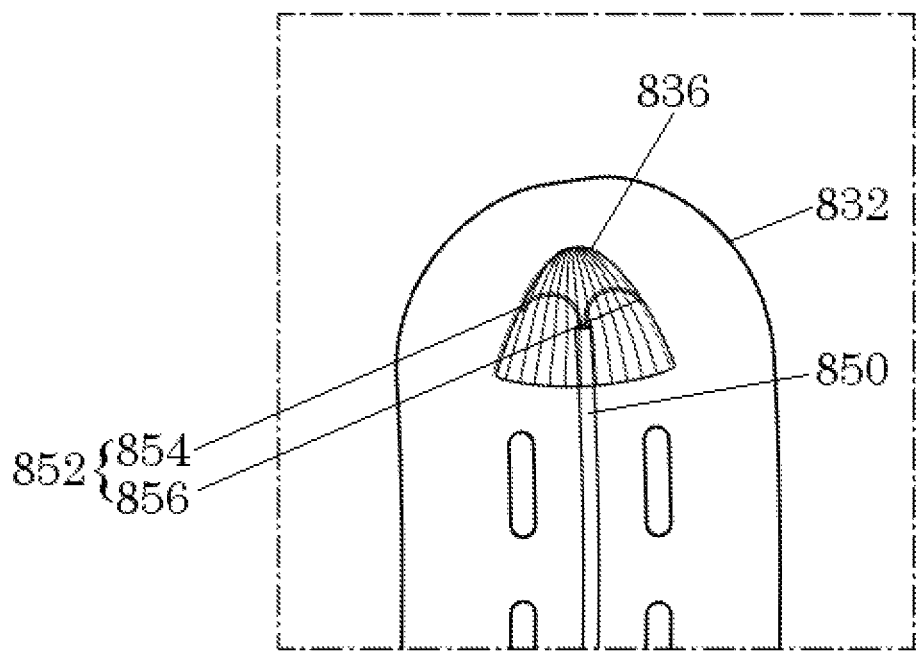
FIG. 15 is a detail view of the locking mechanism of the device of FIG. 14 when the locking mechanism is in the engaged state.
Figure 16:
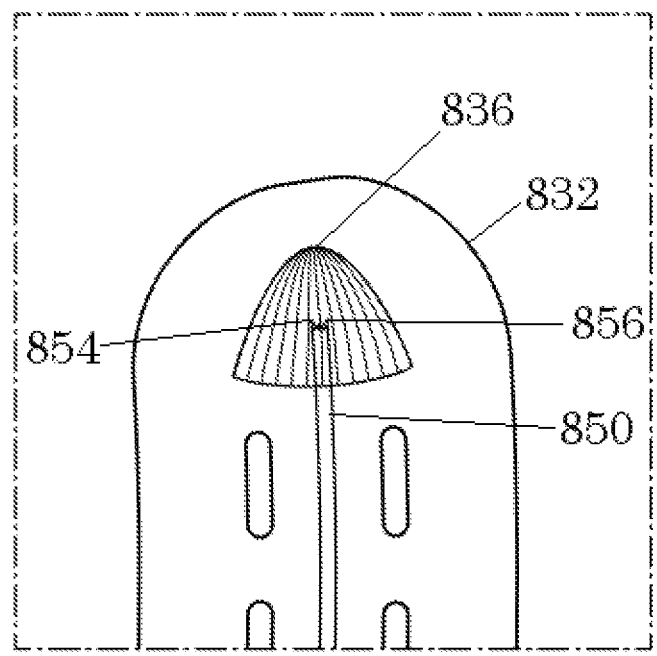
FIG. 16 is a detail view of the locking mechanism of the device of FIG. 14 when the locking mechanism is in the disengaged state.

FIG. 15 shows the device of FIG. 14 with first and second prongs 854 and 856 engaging the interior surface of hood 836 such that the retractable locking wire is locked thereto. FIG. 16 shows the device of FIG. 14 with first and second prongs 854 and 856 disengaged therefrom, so that the retractable locking wire can be removed from the SCS paddle and, if desired, from the surgical site without disturbing the position of the paddle.

Figure 17:
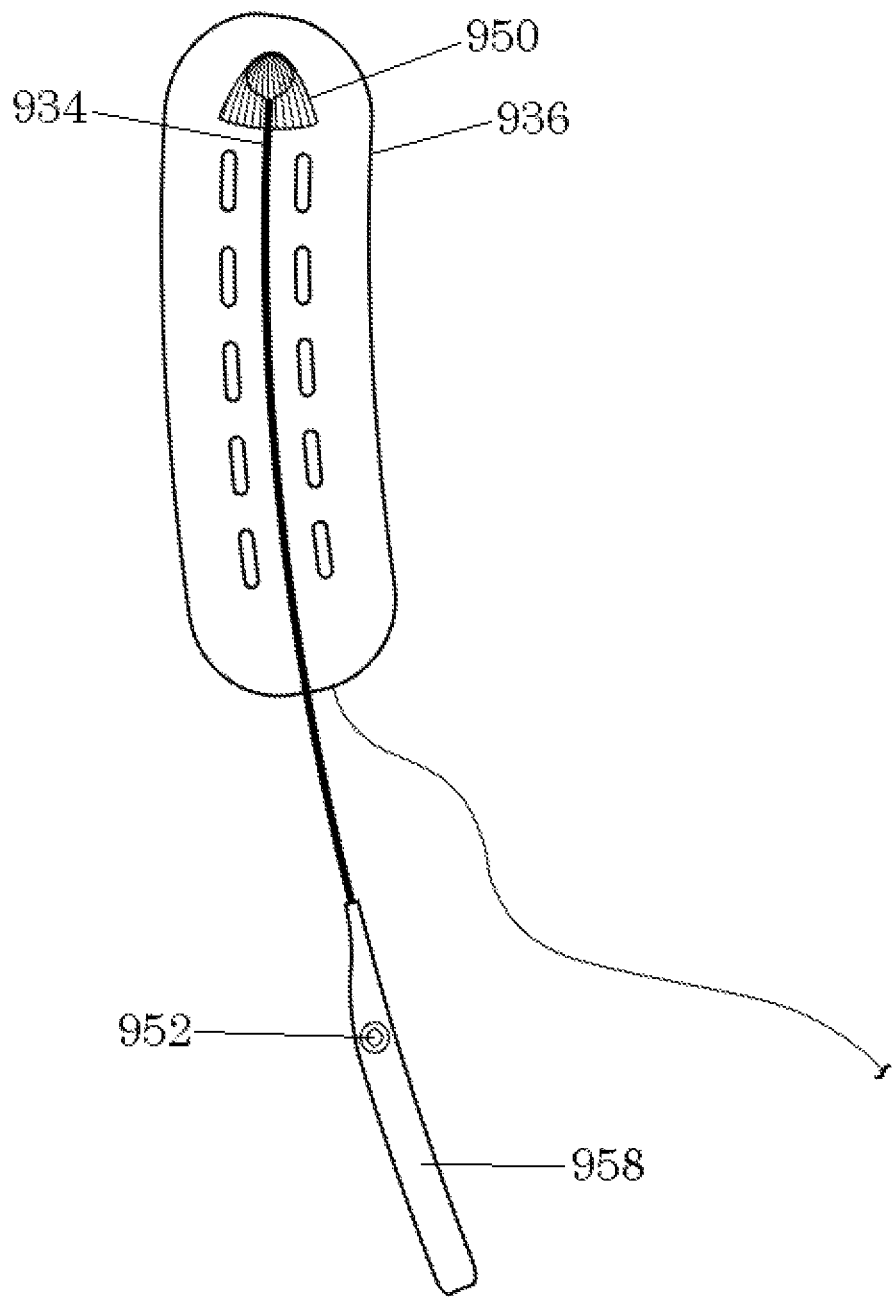
FIG. 17 is a top view of an SCS paddle incorporating one alternative embodiment of a locking mechanism of the present disclosure.

FIG. 17 provides a top view of an embodiment of an SCS paddle lead 932 having an alternative embodiment of a locking mechanism associated therewith. The locking mechanism depicted allows guiding wire 934 to selectively engage and disengage hood 936. When guiding wire 934 is engaged with hood 936, a user may move SCS paddle lead 932 in various directions, including forward, sideways, or rearward, as with the locking embodiment of an SCS paddle described above, without disengaging guiding wire 934 from hood 936, which would cause the user to lose the ability to position the SCS paddle lead as desired or necessary. Once SCS paddle lead 932 is positioned as necessary or desired by the user, guiding wire 934 may be disengaged from hood 936 and the guiding wire removed without disturbing the placement of SCS paddle lead 932.

In the embodiment shown in FIG. 17, guiding wire 934 is preferably hollow and includes an inflatable and deflatable bladder 950 at the end thereof that engages hood 936. Bladder 950 is configured to, when inflated, engage hood 936 securely so that guiding wire 934 may be used to move SCS paddle 932 without disengaging therefrom. The surface of bladder 950, or the interior surface of hood 936, or both, may be scored or otherwise configured to 'grip' one another more securely, though it is contemplated that in some embodiments of the device both surfaces may be smooth.

Control of bladder 950, namely the inflation and deflation thereof, may be accomplished in any suitable manner, and by use of any suitable inflation/deflation mechanism. For example, a physical pump mechanism such as a small bulb, button, or inflating bladder 952 may be provided so that a user of the present device can manually inflate bladder 950 when desired. The bladder 952 may be provided with a valve (not shown) for deflation of bladder 950 when guiding wire 934 is to be disengaged therefrom. Any suitable mechanism for allowing a user to deflate bladder 950 may be used. Alternatively, an automated or electrical pump may be provided with the present device in airflow communication with bladder 950 such that the user of the present device may inflate or deflate the bladder 950 with the simple press of a button, actuation of a switch, computer command, or the like.

The embodiment of SCS paddle lead 932 shown in FIG. 17 includes a handle 958 therewith to allow the user to better manipulate the device, as well as any associated bulb or other inflation/deflation mechanism. In some embodiments, however, the handle may be eliminated.

Figure 18:
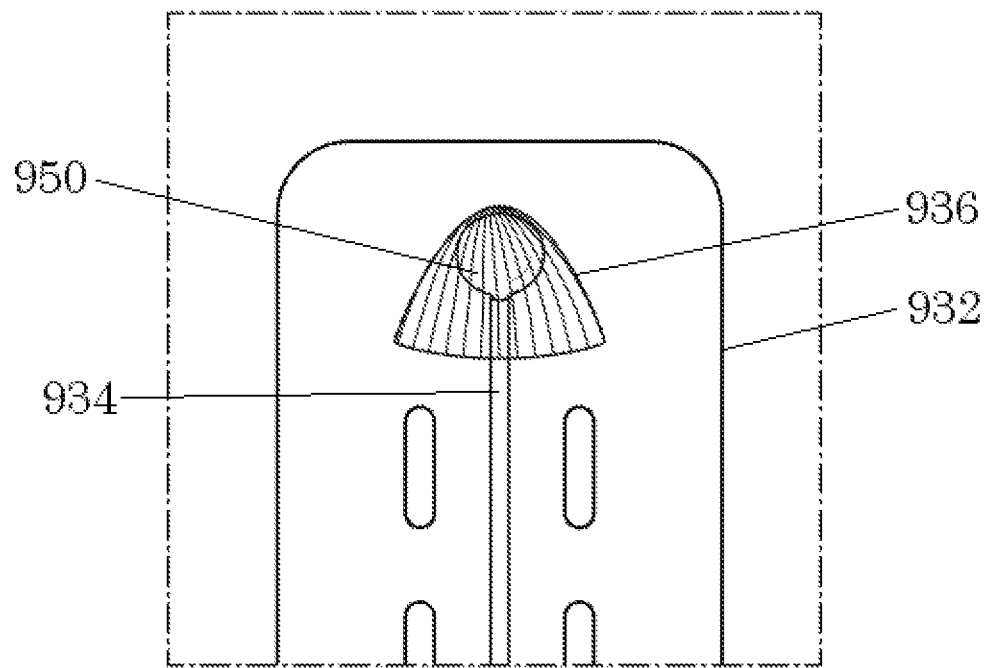
FIG. 18 is a detail view of the locking mechanism of the device of FIG. 17 when the locking mechanism is in the disengaged state.
Figure 19:
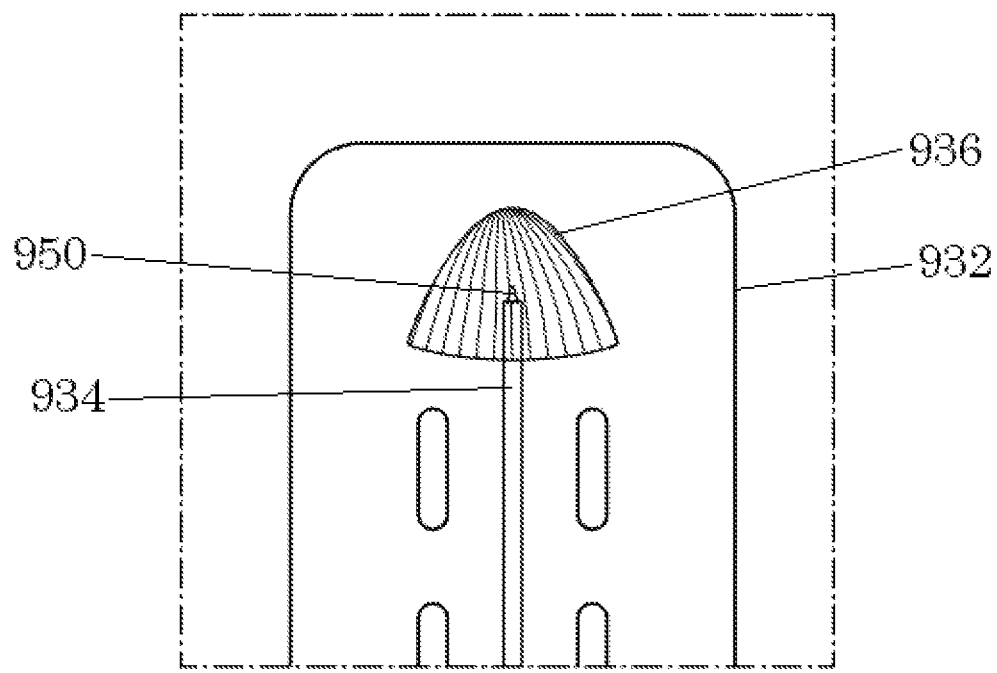
FIG. 19 is a detail view of the locking mechanism of the device of FIG. 17 when the locking mechanism is in the disengaged state.

FIG. 18 shows the device of FIG. 17 with bladder 950 inflated and engaging the interior surface of hood 936. FIG. 19 shows the device of FIG. 17 with bladder 950 deflated and disengaged from hood 936.

Figure 20:
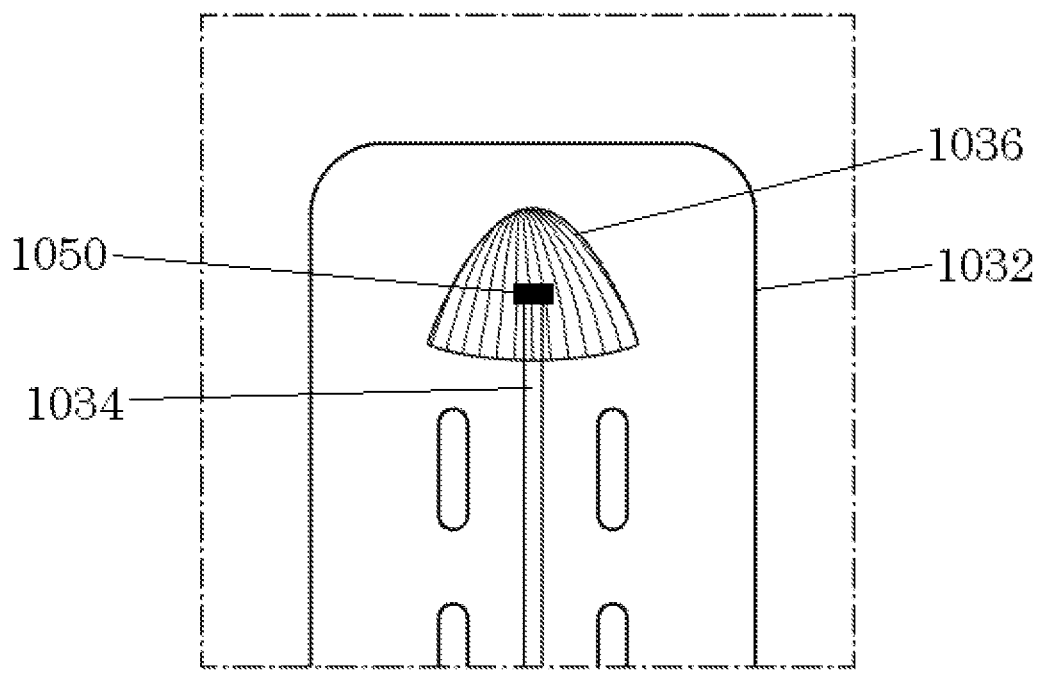
FIG. 20 is depicts an embodiment of the present disclosure wherein the locking mechanism is an electromagnet.

Although the drawings and description above contemplate the use of retractable wires or wire prongs, or an inflatable and deflatable bladder, as the locking mechanisms that allow the guiding wire to be selective engaged or disengaged from the hood of the SCS paddle lead, it is contemplated that any suitable locking/unlocking mechanism may be utilized. Turning to FIG. 20, for example, hood 1036, or a portion thereof, may be constructed from one or more magnetic materials (e.g. ferromagnetic materials). The end of guiding wire 1034 that engages and disengages hood 1036 may include an electromagnet 1050 that may be selectively powered such that guiding wire 1034 engages and disengages hood 1036 when desired. The electromagnet may be powered by the power source utilized by the SCS paddle lead 1032, but is preferably powered by a separate external power source. It is further contemplated that the degree of power provided to the electromagnet may, in some embodiments, be adjusted by the user so that the electromagnet engages the hood of the SCS paddle more strongly or more weakly according to the desires of the user.

It is contemplated that the guiding wires used in accordance with the present disclosure may be made of any suitable material. It is preferred, however, that the guiding wires are radio-opaque, such that they can be imaged during a procedure inserting and properly positioning a lead or paddle within a patient. It is also preferred that the guiding wires have sufficient rigidity to allow steering of a lead or paddle, but that they be malleable enough that a user thereof may shape them as necessary or desired for a given use. It should be understood, however, that some guiding wires may be pre-shaped and relatively rigid, without allowing for easy modification of the guiding wire shape by a user there.

It is to be understood that in the various embodiments of the leads of the present disclosure, the size and shape of the lead, as well as the number and position of various electrodes associated therewith, may be modified according to the needs or desires of a user thereof.

It is to be understood that the foregoing description provides exemplary description of the disclosures herein and is not intended to be limiting. Various modifications to what is described above, or shown in the drawings, will be apparent to those of skill in the art upon reading this disclosure. It is contemplated that such modifications remain within the scope of the present disclosure.

The invention claimed is:

1. A neurostimulation lead comprising:
   a base;
   a plurality of electrodes disposed on said base;
   a steering structure attached to said base; and
   a guiding wire selectively engageable and disengageable with said steering structure, wherein the guiding wire comprises a sheath defining an interior channel along the length thereof; and a retractable locking wire disposed within the channel of the sheath, wherein when the guiding wire is engaged with said steering structure the guiding wire is operable to move said neurostimulation lead in forward, rearward, side-to-side, and downward directions without disengaging said steering structure, and further wherein when said guiding wire is disengaged from said steering structure the guiding wire can be retracted therefrom without disturbing the position of the neurostimulation lead, and further wherein the retractable locking wire is moveable between a first position wherein the retractable locking wire engages the steering structure and the guiding wire thereby engages the steering structure, and a second position wherein the retractable locking wire disengages the steering structure and the guiding wire thereby disengages the steering structure.

2. The neurostimulation lead according to claim 1, wherein the retractable locking wire comprises a forked end comprising a first prong and a second prong.

3. The neurostimulation lead according to claim 2, wherein the actuator is a shaped portion of said first end of said guiding wire capable of manipulation by a user of said neurostimulation lead.

4. The neurostimulation lead according to claim 1, further comprising an actuator at a first end of the guiding wire, wherein said actuator is operable to move the retractable locking wire between the first position and the second position.

5. The neurostimulation lead according to claim 1, wherein the guiding wire comprises an electromagnet at a first end thereof and further wherein the steering structure comprises a magnetic material, wherein the electromagnet is selectively engageable and de-energizable, and wherein when the electromagnet is in the energized state it engages the steering structure, thereby engaging the guiding wire with the steering structure, and when the electromagnet is in the de-energized state is disengages the steering structure, thereby disengaging the guiding wire from the steering structure.

6. The neurostimulation lead according to claim 5, further comprising a power source in electrical communication with said electromagnet, the power source operable by a user of said neurostimulation lead to selectively energize and de-energize the electromagnet.

7. A neurostimulation lead comprising:
a base;
a plurality of electrodes disposed on said base;
a steering structure attached to said base; and
a guiding wire selectively engageable and disengageable with said steering structure, wherein the guiding wire comprises a sheath defining an interior channel along the length thereof; and a tube disposed within the channel of the sheath and extending along the length thereof, wherein the tube comprises a first end comprising a bladder in pneumatic communication with the tube, wherein when the guiding wire is engaged with said steering structure the guiding wire is operable to move said neurostimulation lead in forward, rearward, side-to-side, and downward directions without disengaging said steering structure, and further wherein when said guiding wire is disengaged from said steering structure the guiding wire can be retracted therefrom without disturbing the position of the neurostimulation lead, and further wherein the bladder is selectively inflatable and deflatable, and further wherein when the bladder is in the inflated state the external surface of the bladder engages the steering mechanism, thereby engaging the guiding wire with the steering mechanism, and when the bladder is in the deflated state the bladder disengages the steering structure, thereby disengaging the guiding wire from the steering structure.

8. The neurostimulation lead according to claim 7, further comprising an inflation/deflation mechanism in pneumatic communication with a second end of said tube.

9. The neurostimulation lead according to claim 8, wherein the inflation/deflation mechanism is a bulb comprising a valve, and further wherein the bulb and valve are operable for selective inflation and deflation of the bladder.

10. The neurostimulation lead according to claim 8, wherein the inflation/deflation mechanism is an electrical pump.

* * * * *